United States Patent
Larson et al.

(10) Patent No.: US 6,180,136 B1
(45) Date of Patent: Jan. 30, 2001

(54) PHOSPHOLIPID-COATED MICROCRYSTALS FOR THE SUSTAINED RELEASE OF PHARMACOLOGICALLY ACTIVE COMPOUNDS AND METHODS OF THEIR MANUFACTURE AND USE

(75) Inventors: Kenneth A. Larson, Fort Collins, CO (US); William R. Campbell, Jamestown; Douglas I. Hepler, McLeansville, both of NC (US)

(73) Assignee: Idexx Laboratories, Inc., Westbrook, ME (US)

(*) Notice: Under 35 U.S.C. 154(b), the term of this patent shall be extended for 0 days.

(21) Appl. No.: 09/190,049

(22) Filed: Nov. 10, 1998

(51) Int. Cl.$^7$ .................................................. A61K 9/127
(52) U.S. Cl. ............................ 424/450; 264/4.1; 264/4.3
(58) Field of Search .................................. 424/400, 1.21, 424/9.321, 9.51, 417, 94.3; 436/829; 935/54; 264/4.1, 4.3

(56) References Cited

U.S. PATENT DOCUMENTS

| | | | |
|---|---|---|---|
| 4,497,157 | * 2/1985 | Durr | 53/428 |
| 4,528,193 | * 7/1985 | Ghyczy | 514/78 |
| 4,847,015 | * 7/1989 | Shigematsu | 260/403 |
| 4,874,553 | * 10/1989 | Jorg | 260/403 |
| 4,973,465 | 11/1990 | Baurain et al. | 424/406 |
| 5,091,187 | 2/1992 | Haynes | 424/450 |
| 5,091,188 | 2/1992 | Haynes | 424/450 |

FOREIGN PATENT DOCUMENTS

| | | |
|---|---|---|
| 2 046 094 | 11/1980 | (GB) . |
| 2132736 | 5/1989 | (JP) . |
| WO 96/16643 | 6/1996 | (WO) . |

* cited by examiner

*Primary Examiner*—Gollamudi S. Kishore
(74) *Attorney, Agent, or Firm*—Mary S. Consalvi; Richard San Pietro; Howrey Simon Arnold & White, LLP (57) ABSTRACT

The present invention relates to pharmaceutical compositions for the sustained release of pharmacologically active compounds and methods of their manufacture and use. Sustained release times of 10–12 days have been achieved with the present invention. The present invention provides microcrystal compositions. The microcrystals comprise pharmacologically active compounds and are contained within a phospholipid layer which contains a unique combination of phospholipids. The present invention may be applied to a wide range of pharmaceutical compositions which may be rendered suitable for injection. The microcrystals are of varying sizes. At least 50 percent of the microcrystals are from 0.5 μm to about 3.0 μm in diameter, at least ten percent of the microcrystals are from about 3.0 μm to about 10 μm in diameter, and the composition contains microcrystals which are greater than 10 μm in diameter. In preferred embodiments, at least about 1% of the microcrystals are greater than 10 μm in diameter. The compositions and methods are useful for treating respiratory diseases, infections, inflammation, and pain in a variety of mammals. The compounds and methods are also able to sharply reduce the toxicity of drug compounds.

61 Claims, 5 Drawing Sheets

**Tilmicosin in Animal Tissue
Parts Per Million (by Weight)**

| Tissue | Animal | PPM | Tissue | Animal | PPM |
|---|---|---|---|---|---|
| Lung (1) | Dog | 0.682 | Skin (1) | Dog | 1.072 |
| Lung (1) | Pig | 0.840 | Skin (1) | Pig | 1.063 |
| Lung (1) | Cat | 0.936 | Skin (1) | Cat | 1.057 |
| Lung (2) | Dog | 0.925 | Skin (2) | Dog | 0.822 |
| Lung (2) | Pig | 0.972 | Skin (2) | Pig | 0.848 |
| Kidney | Dog | 0.937 | Skin (2) | Cat | 0.808 |
| Kidney | Pig | 1.036 | Lasissimus Dorsi | Dog | 1.147 |
| Kidney | Cat | 1.112 | Lasissimus Dorsi | Pig | 1.147 |
| | | | Lasissimus Dorsi | Cat | 1.500 |

PHOSPHOLIPID-COATED MICROCRYSTALS FOR THE SUSTAINED RELEASE OF PHARMACOLOGICALLY ACTIVE COMPOUNDS AND METHODS OF THEIR MANUFACTURE AND USE

BACKGROUND OF THE INVENTION

It is known that water insoluble drugs can be rendered injectable by formulating them into aqueous suspensions of phospholipid-coated microcrystals. Haynes, U.S. Pat. No. 5,091,188 and U.S. Pat. No. 5,091,187, disclosed a method of coating pharmaceutical compounds with a phospholipid layer that makes water insoluble drugs able to be contained within an aqueous medium, and therefore suitable for injection in a mammal.

Baurain et al., U.S. Pat. No. 4,973,467 describes the preparation of microcrystals of ginkolide B, kadsurenone, amphotericin B, and nystatin. Baurain et al. prepared microcrystals by the common method of forming a lipid film in a flask by dissolving the lipids to he used in organic solvent, evaporating the solvent, and then sonicating in the presence of the active compound to produce miciocrystals sized between 0.1 $\mu$m and 2 $\mu$m.

Animal husbandry operations which manage large numbers of animals have been unable to realize the benefits of the prior technology because it has not been successfully applied on a large scale. The procedures disclosed by Haynes and others have had limited commercial practicability since the methods involve the use of sonication or other processes which are inappropriate or impractical for producing commercially advantageous quantities of product.

The present invention provides a method suitable for economically producing yields of up to thousands of liters of pharmaceutical compositions for the sustained release of a pharmacologically active compound. The method can be applied with a commercial scale homogenizer, or any instrument or technique which provides the necessary forces to effectively coat the pharmacologically active compound with the lipid suspension.

Furthermore, the compositions of the prior art have relied on commonly available forms of phospholipid mixtures which are highly purified and prohibitively expensive for use on a commercial scale. The present invention discloses a method for isolating a composition of lipids from egg yolk which results in a suspension of lipids which can be economically produced, and can be used to coat a pharmacologically active compound to produce the microcrystals of the present invention. These microcrystals exhibit several beneficial characteristics, including a longer sustained release time and the ability to sharply decrease the toxicity of drug compounds. These microcrystals may be formed into an injectable suspension for subcutaneous injection into a mammal. The suspension may be syringeable and therefore suitable for subcutaneous injection.

One skilled in the art will realize that the microcrystals of this invention can be administered to the mammal in a variety of other ways including, but not limited to, skin patches, ocular inserts, shooting through the skin at high velocity with a medical "air gun," suppositories, or simply providing the compounds in a mammal's food and water.

It has been previously thought that it is desirable to produce a composition of microcrystals having homogeneous microcrystals of a very small size. Previously, it has been believed that it is desirable to produce microcrystals below 1 $\mu$m, or at least below 2 $\mu$m or 3 $\mu$m. The present invention discloses that unexpected benefits, including benefits in timed release delivery, can be realized by producing a composition which contains microcrystals of varying sizes. The present invention discloses compositions wherein at least 50 percent of the microcrytals are from about 0.5 $\mu$m to about 3.0 $\mu$m in diameter, at least ten percent of the microcrystals are from about 3.0 $\mu$m to about 10 $\mu$m in diameter, and the compositions contain microcrystals which are greater than about 10 $\mu$m in diameter. In a preferred embodiment, at least about 50 percent of the microcrystals will be from about 0.5 $\mu$m to about 3 $\mu$m in diameter, from about thirty to about forty percent of the microcrystals will be from about 3 $\mu$m to about 10 $\mu$m in diameter, and the composition contains microcrystals which are greater than about 10 $\mu$m in diameter. We have found that by utilizing microcrystals of these varying sizes sustained release times of as long as 10–12 days can be obtained. The person of skill in the art will readily realize that even presently known lipid compositions may be put into the novel compositions claimed herein to realize these benefits. The invention teaches novel compositions which are mixtures of microcrystals of varying sizes as disclosed herein.

The present invention also di closes methods for treating infections in mammals. In preferred embodiments, methods are provided for treating respiratory diseases in mammals, in particular, infections of the respiratory tract. In particularly preferred embodiments, methods are provided for treating bovine respiratory disease (commonly known as "shipping fever"), kennel cough in dogs, and Potomac fever in horses. In another particularly preferred embodiment, methods are provided for treating infections of the respiratory tract in cats.

Prior methods of treating infections in animals have centered on the regular and repeated administration of antibiotics to the mammal until the infection was eradicated, sometimes by incorporating the drug into the animal's food or water, by oral administration in a paste or with a balling gun, or by repeated injections. Therapeutic regimens often failed due to a failure on the part of the animal owner to follow the prescribed regimen. The present invention provides a method of treating infections which requires only a single administration of the microcrystal compositions of the present invention. The microcrystal composition may be an injectable syringeable suspension. The administration can be delivered by an animal care professional and does not require further participation by the owner for a successful result of the therapy, thereby eliminating issues of therapy noncompliance by the owner as a reason for failure of the therapy. The present methods are applicable to a variety of mammals including, but not limited to, bovines, equines, porcines, caninee, and felines. The person of skill in the art will readily realize that the methods herein disclosed will find applicability to a wide variety of mammals.

The person of skill in the art will also readily realize that the compositions and techniques described herein can be applied to a wide variety of pharmacologically active compounds. Various antibiotics, anesthetics, anti-inflammatory agents, and anti-protozoan agents may all be incorporated into a microcrystal suspension, as may other chemical compounds of varied uses which will be apparent to those of skill in the art.

We have also observed that pharmacologically active compounds which are coated with the phospholipid composition of the present invention are able to attach to blood cells. In this case the pharmacologically active compound is found associated with the blood cells in blood analysis assays. This characteristic of the microcrystals of the present invention serves to facilitate the delivery of pharmacologically active compound to the body tissues.

SUMMARY OF INVENTION

The present invention realizes a substantial advance in the field of microcrystal technology by providing novel lipid compositions for coating microcrystals of useful drugs. These novel compositions result in pharmaceutical suspensions containing phospholipid coated microcrystals which offer significantly longer sustained release times than those of the prior art. These compositions offer the additional and important benefit of sharply reducing the toxicity of many useful pharmaceutical compounds which are underutilized due to concerns about their toxicity.

The present invention also provides new methods for manufacturing suspensions of microcrystals which contain pharmaceutically active compounds Encapsulated in a phospholipid layer on a commercial scale. The suspensions may be made suitable for injection. Various water insoluble and pharmaceutically active compounds may be produced in the form of these phospholipid coated microcryetals. The methods are suitable for producing thousands of liters of microcrystal product, allowing the technology to be utilized on a commercial scale.

The present invention also provides methods for treating infections in a variety of mammals which involve the administration of the microcrystals produced by these methods. In preferred embodiments, the infection may be a bacterial, fungal, protozoa, or any type of parasitic organism which has invaded the body. In a preferred embodiment, the microcrystal suspension may be made into an injectable syringeable suspension and the administration accomplished by subcutaneous injection. These methods offer the distinct advantages of effective single dose therapies to cure infections, eliminate noncompliance as a barrier to drug efficacy, sharply decrease the toxicity of drug compounds, and avoid further stress and discomfort to the treated animal.

The present invention is directed towards novel pharmaceutical compositions for the sustained release of pharmacologically active compounds, and methods of their manufacture. The pharmaceutical compositions contain microcrystals of pharmacologically active compounds which are encapsulated within a phospholipid bilayer. The phospholipid bilayer contains a unique combination of phospholipids which imparts unexpected beneficial properties.

In particular, the present invention provides a composition of lipids used in coating a pharmacologically active compound which is from about 40 percent to about 80 percent by weight of phosphatidylcholine, and from about 10 percent to about 30 percent by weight of phosphatidylethanolamine. In preferred embodiments, the composition will comprise from about 50 percent to about 68 percent by weight phoslhatidylcholine, and from about 15 percent to about 25 percent by wieight phosphatidyl-ethanolamine.

The present invention also provides pharmaceutical compositions which contain a suspension of microcrystals contained within a phospholipid layer which is made of any of the compositions of lipids described above. The microcrystals are a solid, crystalline form of the particular pharmacologically active compound of interest. The suspension may be made suitable for injection into a mammal, and may be made syringeable as well.

The present invention also provides pharmaceutical suspensions of microcrystals which contain a pharmacologically active compound contained within a phospholipid layer. In this aspect, at least about fifty percent of the microcrystals are from about 0.5 μm to about 3.0 μm in diameter, at least about 10 percent of the microcrystals are from about 3 μm to about 10 μm in diameter, and at least about 90 percent of the microcrystals are less than about 10 μm in diameter. The suspension also contains microcrystals which are greater than about 10 μm in diameter. In a preferred embodiment, at least about fifty percent of the microcrystals are from about 0.5 μm to about 3.0 μm in diameter, from about thirty to about 40 percent of the microcrystals are from about 3.0 μm to about 10 μm in diameter, and the suspension contains microcrystals which are greater than about 10 μm in diameter. In a particularly preferred embodiment, at least about 1 percent of the microcrystals are greater than about 10 μm in diameter.

The present invention also provides methods of manufacturing the pharmaceutical compositions of the present invention for the sustained release of pharmacologically active compounds. The compositions contain microcrystals which contain pharmacologically active compounds contained within a phospholipid layer. The method includes the steps of forming a lipid suspension which contains the pharmacologically active compound and passing the lipid suspension with the pharmacologically active compound through a homogenizer at high pressure to coat the compound with the lipid suspension and produce a suspension of microcrystals where at least about fifty percent of the microcrystals are from about 0.5 μm to about 3 μm in diameter, and at least about ten percent of the microcrystals are from about 3 μm to about 10 μm in diameter, and the suspension contains microcrystals which are greater than about 10 μm in diameter. In a preferred embodiment, at least about 25 percent of the microcrystals will be greater than about 3 μm in diameter. In another preferred embodiment, at least about 25 percent of the microcrystals will be from about 3μm to about 10 μm in diameter.

In another aspect, there are provided methods for manufacturing the pharmaceutical compositions of the present invention for the sustained release of pharmacologically active compounds. The compositions contain microcrystals which contain pharmacologically active compounds contained within a phospholipid layer. The methods include the steps of forming a lipid suspension, and contacting the lipid suspension with the pharmacologically active compound to coat the pharmacologically active compound with the lipid suspension and produce a suspension of microcrystals where at least about fifty percent of the microcrystals are from about 0.5 μm to about 3 μm in diameter, and at least about ten percent of the microcrystals are from about 3 μm to about 10 μm in diameter, and the suspension contains microcrystals which are greater than about 10 μm in diameter. In a preferred embodiment, at least about 25 percent of the microcrystals will be greater than about 3 μm in diameter. In other preferred embodiments, at least about 25 percent of the microcrystals will be from about 3 μm to about 10 μm in diameter.

The method produces water insoluble drugs which are coated with the phospholipid suspension and which have been modified such that they can be safely injected and have a sustained release from an injection site in a mammal, and provide an effective therapy for a variety of disease states. The microcrystals can be produced within the above stated size distribution range which serves to increase the sustained release time of the pharmacologically active compound they contain.

In one embodiment of the method, the lipid suspension is passed through a homogenizer repeatedly at high pressure. In a preferred embodiment, it is passed through a homogenizer three times at high pressure. In other embodiments, the lipid suspension may be passed through a homogenizer a number of times necessary to obtain a microcrystal suspension which lacks clumping, contains particles within the desired size ranges indicated above, and is free-flowing.

The pharmacologically active compound may be an antibiotic. The antibiotic may be a cephalone, tilmicosin, or nitazoxanide. The antibiotic may also be a floroauinolone such as ofloxacin, sarafloxicin, or ciprofloxicin. The antibiotic may also be a cephalosporin such as cefazolin, cefuroxine or a derivative of cefuroxine, cefoperazone, or cefoclor. In other embodiments, the antibiotic may be a tetracycline such as oxytetracycline. The pharmacologically active compound may also be a floroquinolone and a cephalosporin which have been combined to form a single molecule. The pharmacologically active compound may also be an anti-inflammatory agent, such as flunixin. In other embodiments, the pharmaceutical composition may be an anesthetic, such as propofal, or an anti-protozoan agent, such as nitazoxanide. The suspension of microcrystals produced by the manufacturing method may also be sterilized with radiation or another sterilization method. In a preferred embodiment, the suspension of microcrystals is sterilized with gamma radiation. Persons of skill in the art will readily see that the techniques and principles disclosed can be applied to a variety of water insoluble pharmaceutical products aid chemicals to produce microcrystals which are useful for a wide variety of purposes. The techniques and principles may also be applied to water soluble compounds which have been modified in order to behave more like water insoluble compounds.

The pharmacologically active compounds described above have formal, chemical names which are hereby provided for reference. Tilmicosin is chemically known as 20-deoxo-20-(3,5-dimethyl piperidinyl)-1-yl desmycosin. Ciprofloxacin is chemically known as 1-cyclopropyl-6-fluoro-1,4-dihydro-4-oxo-7-(1-piperazinyl)-3-quinoline carboxylic acid. Cefazolin is chemically known as [(6R-trans)-3[[5-methyl-1,3,4-thiadiazol-2-yl)thio]methyl]-8-oxo-7-[(1H-tetrazol-1-yl acetyl)-amino]-5-thia-1-azabicyclo[4,2,0]oct-2-ene-2-carborylic acid]. Cefaclor is chemically known as 7-[(aminophenylacetyl)amino]-3-chloro-8-oxo-5-thia-1-azabicyclo[4,2,0]oct-2-ene-2-carboxylic acid. Cefoperazone is chemically known as 7-[D-(−)-α-(4-ethyl-2,3-dioxo-1-piperzine carboxamido)-α-( 4-hydroxylphenyl) acetamido]-3[[1-methyl-1H-tetra-zol-5-yl) thio]methyl]-3-cephem-4-carboxylic acid. Cefuroxine is chemically known as [6R-[6α, 7β(Z)]]-3-[[(aminocarbonyl)oxy]methyl]-7-[[2-furanyl(methoxyimino)acetyl]amino]- 8-oxo-5-thia-1-azabicyclo[4,2,0]oct-2-ene-2-carboxylic acid. Oxytetracycline is chemically known as 4-(dimethylamino)-1,4,4a,5,-5a,6,11,12a-octahydro-3,5,6,10,12,12a-hexahydroxy-6-methyl-1,11-dioxo-2-naphthalenecarboxamide. Ofloxacin is chemically known as (±)-9-fluoro-2,3-dihydro-3-methyl-10-(4-methyl-1-piperazinyl)-7-oxo-7H -pyrido-[1,2,3-de]-1,4-benzoxazine-6-carboxylic acid. Flunixin is chemically known as 2-[[2-methyl-3-(trifluoromethyl)phenyl]amino]-3-pyridine carboxylic acid. Propofal is chemically known as 2,6-bis(1-methylethyl)phenol. Cephalone (cephaquinolone) is chemically known as 7[(1-cyclopropyl-6-fluoro-7-(4-ethyl piperazine-1-yl-1-, 4 dihydro-4-oxoquinoline-3-yl) carboxamido]cefilosporanic acid. Nitazoxanide (NTZ) is chemically known as 2-(acetyloxy)-N-(5-nitro-2-thiazolyl) benzamide. Saraloxacin is chemically known as 6-Fluoro-1-(4-fluorophenyl)-1,4-dihydro-4-oxo-7-(1-piperazinyl)-3-quinolinecarboxylic acid.

The present invention also provides a method for treating an infection in a mammal. The method contains the steps of administering to the mammal an effective dose of a suspension containing microcrystals which contains a pharmacologically active compound within a phospholipid layer. At least about 50 percent of the microcrystals are from about 0.5 μm to about 3 μm in diameter, at least about ten percent of the microcrystals are from about 3 μm to about 10 μm in diameter, and the suspension contains microcrystals that are greater than about 10 μm in diameter. In a preferred embodiment, at least about 25 percent of the microcrystals will be from about 3 μm to about 10 μm.

In preferred embodiments, the pharmacologically active compound may be any of the pharmacologically active compounds described herein.

In a preferred embodiment, the infection may be a respiratory disease and may be treated with microcrystals containing any of the above named compounds. In a particularly preferred embodiment, the infection may be bovine respiratory disease and the pharmacologically active compound may be oxytetracycline. In another particularly preferred embodiment, the disease may be "kennel cough," the mammal a canine, and the pharmacologically active compound tilmicosin.

The infection may also be caused by a protozoa and the microcrystal may contain an anti-protozoa agent such as nitazoxanide (NTZ). The infection may also be caused by a fungus and the pharmacologically active compound contained in the microcrystal may be an anti-fungal agent. The person of skill in the art will readily see that the microcrystals may contain a wide variety of pharmacologically active compounds which may be used to treat a wide variety of diseases.

In preferred embodiments, the suspensions of the present invention may be made into an injectable syringeable form and administered to the mammal by parenteral administration. The mammal may be a bovine, an equine, a porcine, a canine, a feline, or any mammal.

In another aspect, the invention provides a method for treating inflammation in a mammal. In this aspect, the pharmacologically active compound will be an anti-inflammatory agent contained within a phospholipid layer. In a preferred embodiment, the anti-inflammatory agent may be flunixin.

In another aspect of the invention, the above method may be a method for treating pain in a mammal. In this aspect, the microcrystals contain an anesthetic. In a preferred embodiment, the anesthetic may be propofal. All of the pharmaceutical compounds described herein may be made into a syringeable injectable form and administered to the mammal parenterally.

The present invention also provides a method for isolating from a lipid source a composition of lipids suitable for coating microcrystals. The method includes the steps of performing a lipid extraction on the lipid source with acetone, and a lipid extraction on the lipid source with ethyl alcohol. In a preferred embodiment, the lipid source is egg yolk.

The present invention also provides a pharmaceutical composition which contains microcrystals, which are compositionally from about 10 percent to about 30 percent by weight of a pharmacologically active compound, and from about 15 percent to about 30 percent of a phospholipid syrup. In a preferred embodiment, the microcrystals may be compositionally from about 25 percent to about 30 percent by weight of a pharmacologically active compound, and about 20 percent of a phospholipid syrup. In a preferred embodiment, the pharmacologically active compound may be an antibiotic, such as oxytetracycline. In other embodiments, the pharmacologically active compound may be any of the compounds described herein.

The person of skill in the art will realize that the techniques and principles disclosed can be used to treat a variety of diseases in many types of mammals.

DETAILED DESCRIPTION OF THE INVENTION

The present invention relates to a new technology for the manufacture of sustained release pharmaceutical compositions, particularly as applied to water insoluble drugs in a veterinary context. The compositions may be provided as suspensions in an injectable syringeable form. The invention provides for the manufacture of microcrystals which contain from about 10 percent to about 30 percent (w/v) of an antibiotic or other pharmacologically active compound as the active ingredient, and from about 15 percent to about 30 percent (w/v) of phospholipids syrup as dispersing agent. The suspension products may be terminally sterilized by gamma radiation. In a preferred embodiment the suspension may contain microcrystals which contain from about 25 percent to about 30 percent (w/v) of a pharmacologically active compound (OTC), and about 20 percent (w/v) phospholipids syrup. In a preferred embodiment, the pharmacologically active compound is oxytetracycline (OTC). (We have found that this higher percentage of OTC results in a more concentrated depot of medication which has resulted in a longer release time for the drug into the blood of the treated animal. We have also found that the higher concentration of OTC enables the use of a smaller volume of pharmaceutical suspension, thus decreasing stress on the animal.

The antibiotic-containing suspensions are sustained release formulations which are effective fox the treatment of various diseases. There are provided methods for the manufacture of suspensions containing microcrystal which contain numerous antibiotics, including tilmicosin, cephalone, ofloxacin, cefazolin, cefuroxine and its derivatives, cefoperazone, cefaclor, sarafloxicin, NTZ, and ciprofloxicin. Other methods are provided for the manufacture of microcrystals which contain anti-inflammatory agents such as flunixin, anesthetics such as propofal, and anti-protozoan agents such as nitazoxanide. The suspensions may be provided in a syringeable injectable form. The dose may be calculated on a per pound basis. The suspension dose may be administered subcutaneously per injection for the required number of injections in different skin regions per treatment. In cows, more than one injection may be required, whereas in other mammals such as dogs, cats, or pigs a single injection of the antibiotic may be effective to achieve the therapeutic objective. The injection(s) can provide therapeutic tissue levels of pharmacologically active compound over periods of up to 10–12 days.

Water insoluble drugs may be tendered injectable by formulating as aqueous suspensions of phospholipid-coated antibiotic microcrystals for veterinary subcutaneous administration. The membrane phospholipid stabilizes the microcrystals by both hydrophobic and hydrophilic interactions.

We have also unexpectedly found that the microcrystals of the present invention offer the additional advantage of sharply reducing the toxicity of certain pharmacologically active compounds, rendering these compounds safe to use. For example, there has been a great hesitancy to use drugs such as tilmicosin and flunixin because of their known toxic effects. Similar concerns surround the use of oxytetracycline in horses and cows. We have unexpectedly found that tilmicosin and flunixin can be safely injected into cats, dogs, and pigs when they are coated with the phospholipid compositions of the present invention. Oxytetracycline can also be rendered much safer for horses and cows when coated with these compositions. Therefore, the present invention makes available to the animal caretaker drug products which were formerly underutilized die to concerns over animal safety. The present invention also provides a new tool to animal caretakers dealing with resistant strains of organisms since previously underutilized antibiotics can be used with greater confidence.

Effects of Utilizing a Range of Microcrystal Sizes

An important aspect of the present invention is the fact that homogenization at high pressure of solid particles of pharmacologically active compounds such as antibiotics or other drugs, with a lipid suspension produces a thorough and complete coating of the solid particles with the lipid suspension. We have unexpectedly found that if the homogenization processing is stopped at a point where the microcrystals exist in a range of particle sizes, a suspension can be produced which offers the benefit of longer release times when injected into mammals. It was previously believed that it was desirable to produce microcrystals in the size range of 0.1 $\mu$m to 3 $\mu$m, with a preference for microcrystals below 1 $\mu$m in diameter. However, we have unexpectedly found that longer release times can be obtained by stopping the homogenization process at a point when more than at least about 50 percent of the microcrystals are from about 0.5 $\mu$m to about 3.0 $\mu$m in diameter, at least about ten percent of the microcrystals are from about 3 $\mu$m to about 10 $\mu$m in diameter, and at least about 90% of the microcrystals produced are less than about 10 $\mu$m in diameter. In preferred embodiments, at least about 50 percent of the microcrystals are from about 0.5 $\mu$m to about 3 $\mu$m in diameter, from about 3.0 percent to about 40 percent of the microcrystals are from about 3.0 $\mu$m to about 10 $\mu$m in diameter, and the suspension contains microcrystals which are greater than about 10 $\mu$m in diameter. In a particularly preferred embodiment, at least about one percent of the microcrystals are greater than about 10 $\mu$m in diameter. We have unexpectedly found that the release times of diffusion from an injection "depot" into the blood to the infection site by the pharmacologically active compounds contained by the microcrystals can be increased by obtaining suspensions which contain microcrystals of these varying sizes.

While not wanting to be bound by any particular theory or principle, it is also believed that the unique lipid composition disclosed herein may play an important role in realizing the sustained release times we have obtained. It is also thought that it may be a combination of the unique particle sizes and the novel lipid compositions of the present invention which combine to enable the realization of these benefits.

Longer Treatment Intervals

The longer sustained release times which have been attainable with the compositions and methods of the present invention result in important advantages. We have achieved sustained release times of 10–12 days in cattle and 7 days in dogs, cats, and swine. Dogs and cats can be treated with a single administration thus eliminating issues of therapy noncompliance by owners, a major reason for failure of a therapeutic regimen. Cattle can be treated once every 10–12 days as opposed to presently available methods and compounds which require treatment at intervals of about 3–5 days. Therefore, the present invention offers the additional benefit of cost savings to the animal owners and substantially decreased stress on the animals, which are treated at less frequent intervals, or a single time.

Therefore, using the compositions and methods disclosed herein, we have been able to realize the useful benefits of microcrystal technology, and have shown the efficacy of these novel pharmaceutical products and obtained release times longer than any others thus far available. Since homogenization can be conveniently practiced on a large scale using industrial-sized homogenizers, this invention makes available methods of producing microcrystals of useful pharmacologically active compounds on a large, commercially viable scale where up to thousands of liters of material can be conveniently and economically produced.

In the manufacturing process, the temperature of the suspension increases during homogenization. We have found that the consistency of the suspension is not acceptable at a processing temperature greater than 60° C., and preferably should be processed below 50° C.

In a preferred embodiment of the invention, the suspension contains microcrystals of oxytetracycline. This suspension is very useful for the treatment of bovine respiratory disease. The person of skill in the art will realize that the principles and techniques disclosed herein can be applied to a variety of compounds in many contexts. Even water soluble compounds can be chemically modified so as to behave more like water insoluble compounds. This can be accomplished by a change in pH or by covalent modification of the molecule or by complexation with various molecules which are used in the art to decrease the water soluble properties of a molecule. The person of ordinary skill will realize that the principles and techniques described herein will also find application to some Water soluble compounds which have been modified so as to chemically behave more like water insoluble compounds, and will know of various methods which are available to modify water soluble compounds to make them chemically behave more like water insoluble compounds.

The Homogenizer

We have achieved success in manufacturing the microcrystals of the present invention with a homogenizer from APV Gaulin Rannie, Wilmington, Massachusetts, Model MS18-10TBS, which was operated according to the manufactufer's instructions. We were unable to achieve the desired level of coating of microcrystals with homogenizers of other manufacturers which operate according to a principle of agitation with a probe with blades and stirring.

While not wanting to be bound by a single theory or operating principle, it is believed that the properties of the homogenizer which are needed to successfully conduct the method are that the suspension is forced through a very small aperture under pressure, as opposed to those homogenizers which work according to a "chop and blend" principle. It is believed that the shear forces generated by the pressures involved combined with the forcing of the crystalline particles through the small aperture facilitates the coating of the crystalline form of the pharmacologically active compound with the composition of phospholipid syrup. In a preferred embodiment, the process is conducted with pressures of above 10,000 psi which reduces the size of the microcrystals. In embodiments where the suspension will be injected into the mammal, it is important that the homogenizer produce a material which is flowable, lacks clumps, and contains microcrystals in the size ranges disclosed herein. As we have stated, in a preferred embodiment, the homogenizer produces microcrystals which are of a variety of sizes, at least about 90% of which are less than about 10 $\mu$m in diameter. More than about 50 percent of the microcrystals will be from about 0.5 $\mu$m to about 3 $\mu$m in diameter, and the composition will contain microcrystals greater than about 10 $\mu$m in diameter. In preferred embodiments, a substantial portion, usually from about 30 percent to about 40 percent will be from about 3 $\mu$m to about 10 $\mu$m in diameter. In another particularly preferred embodiment, approximately 1–2%, will be greater than about 10 $\mu$m in diameter. This range of sizes is very beneficial for obtaining longer sustained release times than have been previously available. As the homogenizer forces the material through the apertures and breaks up any clumps which are present, it also coats the solid particles with the lipid composition. Any homogenizer which operates according to the same principles as the Gaulin Homogenizer should produce microcrystals which can be effectively used to practice the present inventions.

A person of skill in the art will realize that other instruments operating under a variety of principles may be used to produce the microcrystals described herein, as long as they produce a suspension which is flowable, lacks clumping, thoroughly coats the microcrystals with the lipid composition, and are able to produce microcrystals of the sizes described herein. Useful, though not optimal microcrystals may also be obtained by utilizing the novel lipid composition described above with microcrystals described in the prior art. However, the benefit of being able to economically produce microcrystal suspensions on a commercially viable scale will be realized, as well as sustained release times which may be realized with the novel lipid composition disclosed herein.

Other benefits are also obtainable with the compositions and methods of the present invention. We have found that microcrystals of the present invention are able to be taken up by or attach to blood cells. While not wanting to be limited or bound by any particular theory, it is believed that the phospholipid compositions of the present invention enables the crystalline drug compounds to be taken up by or associated with blood cells by either being recognized by the blood cell as a compound to be taken into the cell, by associating with or becoming embedded within the cell membrane, or by van der Waals forces. It may be that the microcrystals become associated with the blood cells by a combination of these factors, or by other, presently unknown factors. However, the microcrystals of the present invention are associated with blood cells in blood analysis assays.

The invention is further illustrated through the following examples. These examples are not intended to be limiting. The person of skill in the art will realize that these techniques can be applied to a variety of compounds in various contexts.

EXAMPLE 1

The lipid composition of the present invention contains a particular mix of phospholipids. We have found that increased sustained release times may be obtained by using this phospholipid composition. The phospholipid composition of the present invention can be derived from egg lecithin. The composition contains phosphatidylcholine and a substantial amount of phosphatidylethanolamine. It also contains other lipids such as steroids, di- and tri- glycerides, and other fatty acids. The present method allows for the extraction of a lipid mixture which is useful for practicing the present invention at a cost which is substantially less than those previously available.

To extract the phospholipid mixture which may be employed in the present invention, we performed a lipid extraction procedure which began with dehydrated yolk from chicken eggs. The yolk material was extracted once with acetone, followed by one extraction with ethyl alcohol. The solvents were removed and the remaining syrup was analyzed by gas chromatography/mass spectroscopy. Of the syrup obtained, 90% was found to be solids.

Approximately 70% of the phoslholipid syrup material was lipid. At least 50% of the lipids were phosphatidylcholine and at least 15% was phosphatidylethanolamine. The remainder were other lipids. While these are typical compositions, more or less of these materials may be present. For example, we found that phosphatidylcholine sometimes comprised up to 68% of the lipid material, and phosphatidylethanolamine can comprise as little as 10% or 15% or as much as 25% of the lipid material. The actual amounts may vary depending on a variety of factors which are normal and expected in chemical processes, such as the technique of the operator.

EXAMPLE 2

This example illustrates the method whereby microcrystals containing oxytetracycline were prepared.

The formula for making the microcrystals was as follows:

| | |
|---|---|
| oxytetracycline (OTC) | 25% w/v |
| phospholipid syrup (from Example 1) | 20% w/v |
| mannitol USP | 2.25% |
| methylparaben NF | 0.18% |
| propylparaben NF | 0.02% |
| Water for Injection | QS |

Figure 1:
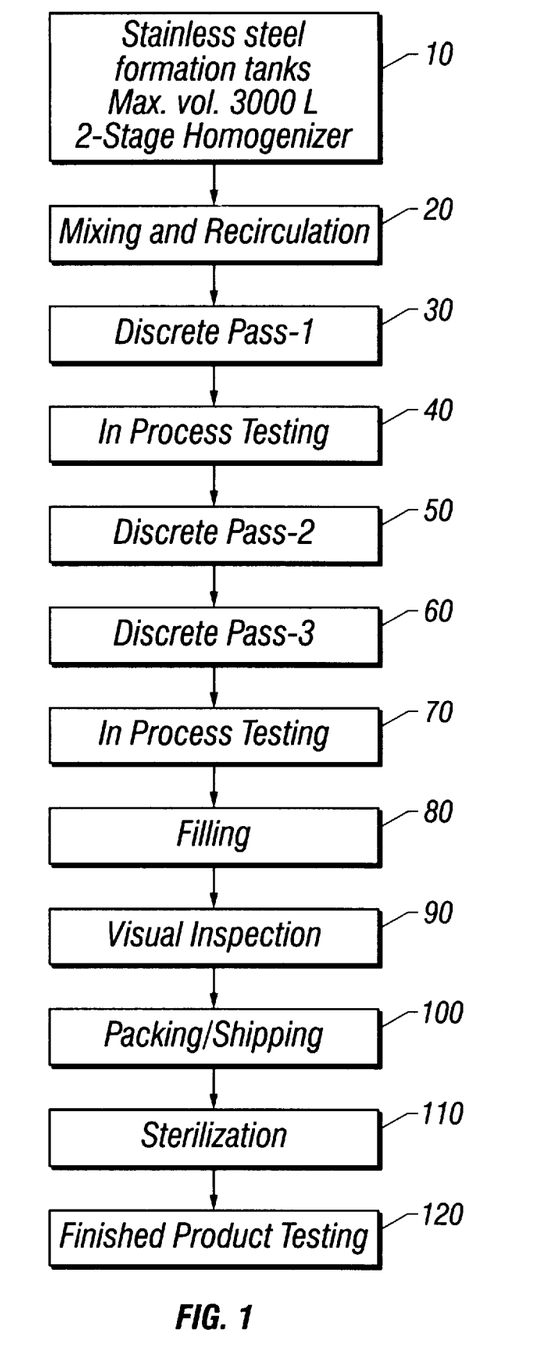
FIG. 1 is a schematic drawing of the process of manufacturing injectable syringeable pharmaceutical suspension for the sustained release of pharmacologically active compounds of the present invention.

Referring to FIG. 1 throughout this example, water for injection (WFI) USP, was added to a 3,000 L stainless steel formulation tank to approximately 40% of target final tank batch volume at a temperature of not more than 32° C. (10). Mannitol USP was added and the ingredients mixed until the mannitol dissolved. WFI was then added to 45% of final tank batch volume, and the solution mixed for at least 10 minutes. Mannitol was tested for and whenever necessary, increments of mannitol or WFI were added to achieve a final mannitol concentration of 2.25% (w/v). Suspension recirculation was then initiated (20).

Methylparaben NF, propylparaben NF, phospholipids syrup (see Example 1), and oxytetracycline were added with continuous recirculation. The solution was mixed for a minimum of 30 minutes until the suspension appeared to be creamy without any clumps of raw material. WFI was added to the target final batch volume and mixed for at least 15 minutes. We note that the mannitol and paraben were first mixed with WFI using less than the total expected amount of water. We then added the phospholipids syrup which went readily into solution. The OTC powder was then blended into this liquid. We then QS'ed the final volume of water to have a complete "pre-mix" for processing through a Gaulin Homogenizer for three complete passes, as explained below (20).

The suspension was cooled to not more than 70° F. Discrete pass 1 (30) was performed by passing the suspension from one mixing tank through the homogenizer into a second mixing tank at 10,000 psi (stage 1 valve) and 500 psi (stage 2 valve). The pH may be measured and adjusted if necessary with 10N sodium hydroxide and/or 5 N HCl. The formulation may be tested for oxytetracycline and adjusted if necessary (40).

The solution is again cooled to not more than 70° F. Discrete pass 2 (50) is performed by passing the suspension from one mixing tank through the homogenizer into the second tank at 10,000 psi (stage 1 valve) and 500 psi (stage 2 valve).

The suspension was cooled to not more than 70° F. Discrete pass 3 (60) was performed by passing the suspension from one mixing tank through the homogenize, into the second tank at 10,000 (stage 1 valve) and 500 psi (stage 2 valve). The pH may then be measured and adjusted with 10N sodium hydroxide and/or 5 N HCl, if required (70).

The suspension is aliquoted into containers of appropriate size (80), visually inspected (90), packed for shipping (100), and may be sterilized by gamma irradiation (110). We have found that, in the case of oxytetracycline, it is desirable to use from 20 kilogreys to 40 kilogreys of radiation to accomplish the sterilization procedure. Finished product testing may then be performed (120). The process here disclosed produces phospholipid-coated microcrystals containing antibiotic in an aqueous suspension. In the case of oxytetracycline, the drug is administered once to produce therapeutic blood and tissue levels of oxytetracycline for 12 days in cows.

While this example illustrates the manufacture of oxytetracycline on a large scale, the same principles can be followed to produce microcrystals of various pharmacologically active compounds. The person of skill in the art will understand that minor modifications to this technique may be required for other compounds.

EXAMPLE 3

This example illustrates the injection of various dosages of microcrystals containing OTC into cattle and the levels of OTC achieved in serum and lung tissue. Sustained release of OTC and tissue residue depletion data are also illustrated.

Figure 2:
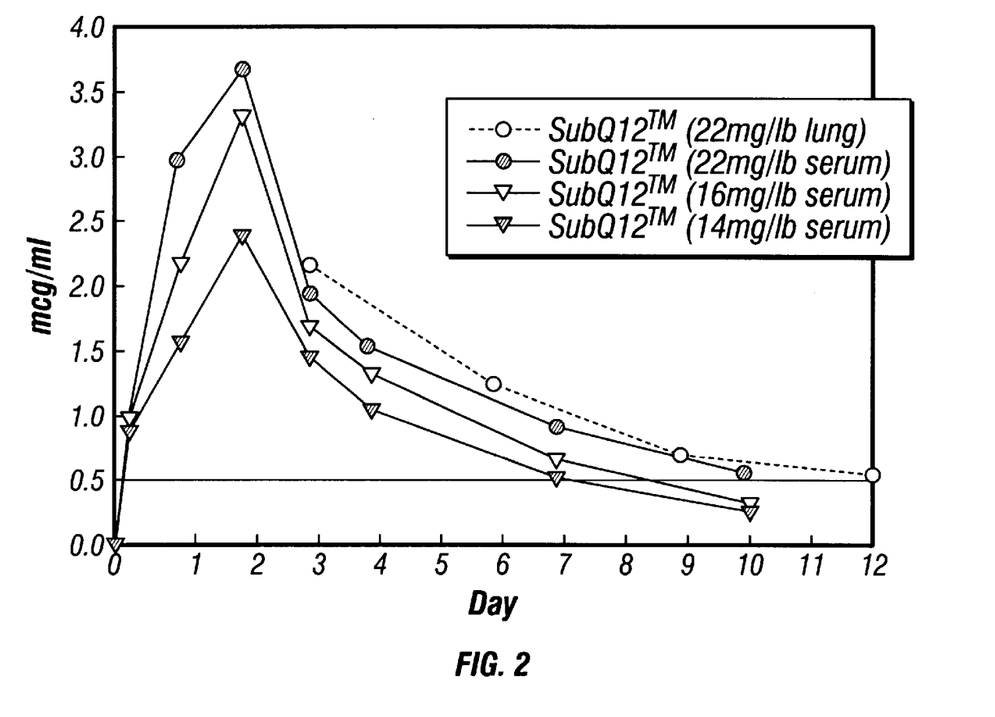
FIG. 2 is a graphical illustration the mean serum and lung tissue concentrations in cows of OTC as a function of time.

A sample of an oxytetracycline microcrystal suspension was manufactured in accordance with Example 2, and potency was measured at 250 mg/ml. Suspension formulation dosages of 22 mg/lb animal weight, 16 mg/lb, and 10 mg/lb were subcutaneously injected into healthy beef cattle which weighed from 734–764 lbs. FIG. 2 shows the mean serum and lung tissue concentrations of OTC as a function of time. The OTC blood concentrations reached peak levels of 3.7 ppm at 54 hrs. Depletion rates appeared fairly similar among the dosage levels. Even at 10 days post-dose there were relatively significant serum OTC concentrations; 0.2, 0.3 and 0.6 ppm for the 10, 16 and 22 mg/lb dosages, respectively.

We also examined tissue residue depletion of OTC administered subcutaneously in healthy calves at a target dose rate of 22 mg OTC/lb body weight in order to determine whether effective quantities of the drug were actually present in body tissue. Group average body weights on the day of drug treatment were between 587–632 lbs. Lung tissue levels averaged 2.18 ppm at 3 days withdrawal and declined progressively through the last sampling point at 12 days postdose, when levels averaged 0.55 ppm.

We therefore unexpectedly found serum OTC concentrations at effective levels as late as 10 days post-dose, several days longer than those attainable with previously known compositions.

The following examples illustrate that the compositions of the present invention have the ability to sharply reduce the toxicity of drugs. Tilmicosin is generally not used in dogs, cats, or pigs, because of concerns about the toxicity of this drug compound. Treatment of these animals with effective doses of tilmicosin may result in the death of these animals. Flunixin is generally not used in cats, also because of concerns over toxicity. Flunixin is sometimes used with hesitancy in dogs, but is also surrounded by the same toxicity concerns. It is noted that treatment of these animals with dosages of only one-half of those described below is capable of causing the death of these animals.

EXAMPLE 4

Use of Oxytetracycline Microcrystals in Horses

This example illustrates that microcrystals containing 25% oxytetracycline were safely injected into horses at a dosage as high as 16 mg/lb.

While oxytetracycline is commonly used to treat Potomac fever in horses, the administration of OTC in horses presents the danger of killing the animal if the drug is administered too quickly, as OTC may interact with and lyse the white blood cells and cause severe shock in the animal. Therefore, there exists a need for a safer mode of administering medications of this type to horses and other mammals.

25% OTC microcrystals were injected subcutaneously and intra-muscularly into healthy horse. This was found to cause temporary sore muscles in the horses, but no other adverse effects were observed. Therapeutic levels of OTC will be observed for up to 10 days.

25% OTC microcrystals were also administered intravenously into horses at a dose of 14 mg/lb. No adverse effects were observed with this mode of administration, and statistical extrapolation revealed therapeutic levels of OTC will remain in the blood for at least five days.

25% OTC microcrystals were also administered intravenously at a dose of 16 mg/lb. No adverse effects were observed, and this dose will provide therapeutic levels of OTC for over five days.

While not wanting to be bound by any particular theory or principle, it is believed that the lipid coating of the microcrystal composition serves to form a protective barrier and protect the labile white blood cells from the OTC.

EXAMPLE 5

The small scale manufacture of tilmicosin is illustrated in Example 9 below. Tilmicosin can also be manufactured on a large scale by following the principles taught in the examples above.

This example discusses the results of injecting microcrystals containing tilmicosin into dogs, cats, and pigs and the subsequent analysis of body tissues for tilmicosin content. It is illustrated that another benefit of the present invention is that compounds which are otherwise too toxic to be safely administered to animals can be safely administered after being coated with the phospholipid compositions of the present invention. In the present embodiment, the invention enables the animal caretaker to take advantage of this very effective antibiotic.

Figure 3:
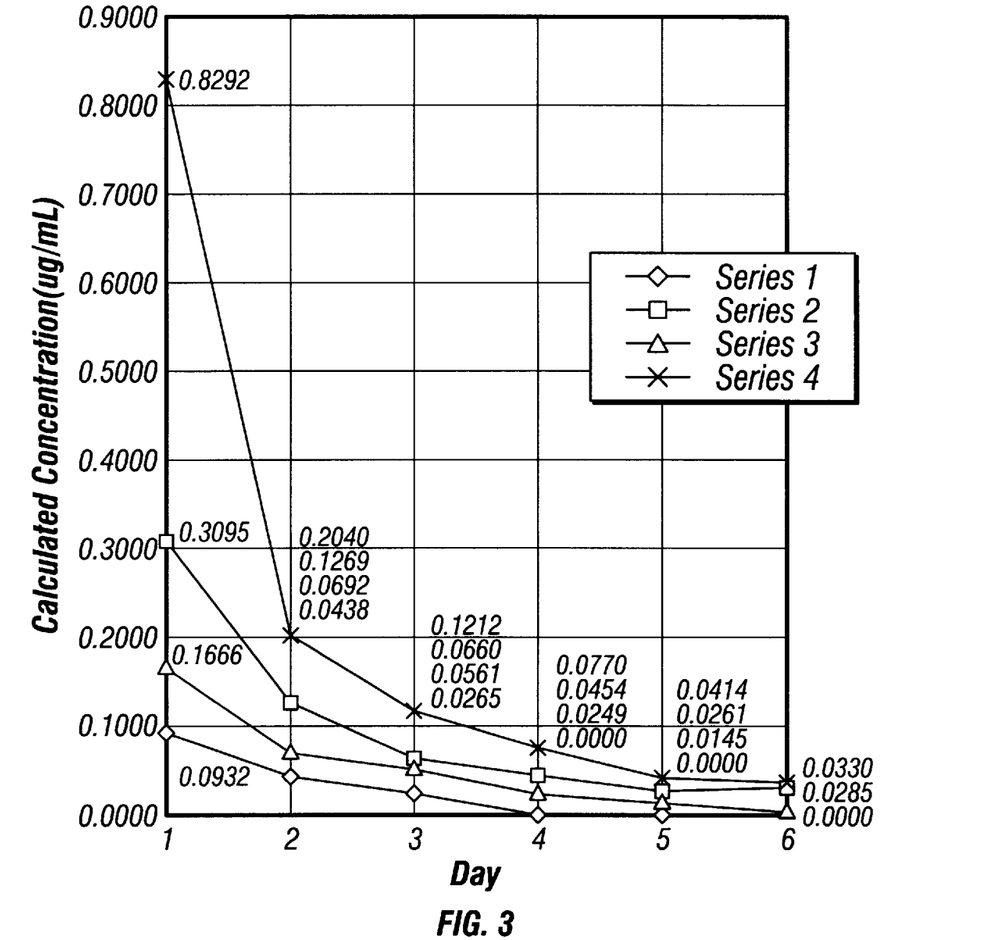
FIG. 3 is a graphical illustration of levels of tilmicosin in the blood serum in dogs after administration of 20 mg/kg of microcrystals containing tilmicosin.
Figure 4:
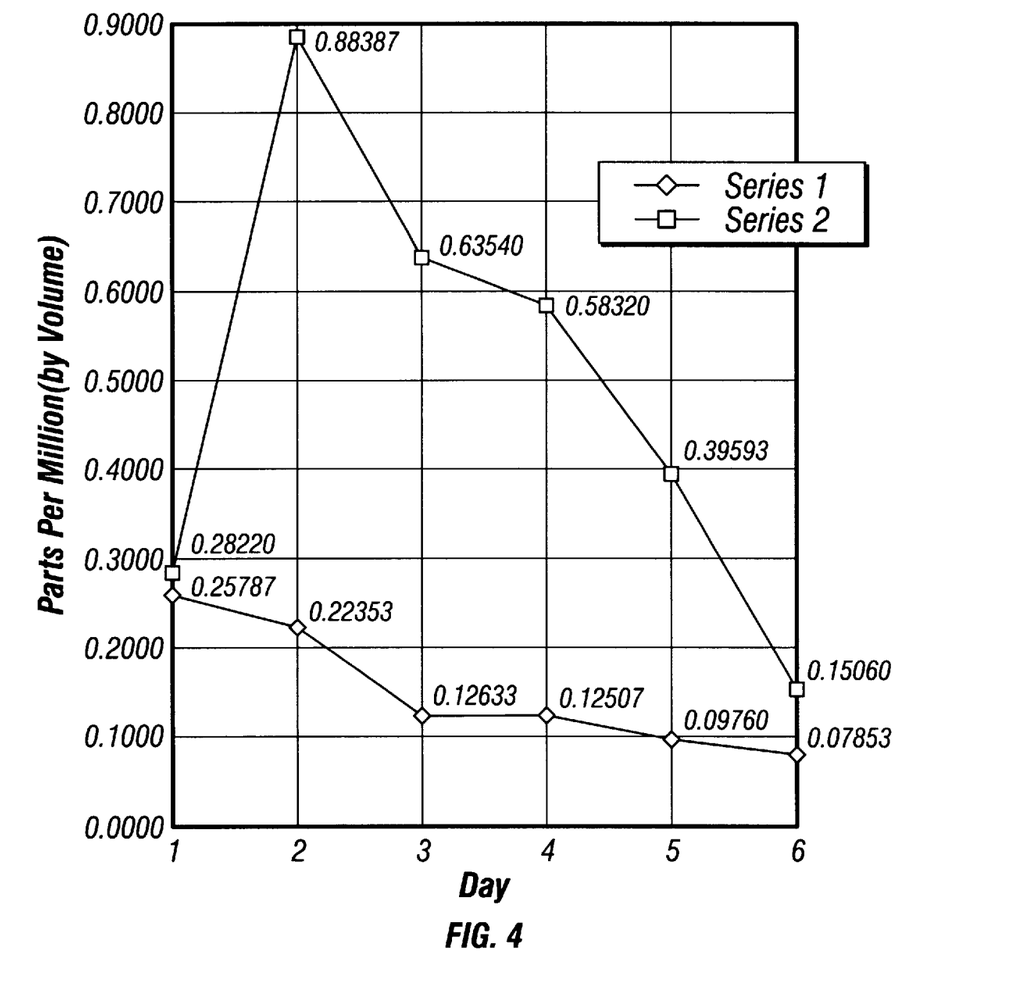
FIG. 4 is a graphical illustration of levels of tilmicosin in the blood cells of dogs after administration of 20 mg/kg of microcrystals containing tilmicosin.

Two dogs (1 male and 1 female) were injected subcutaneously with microcrystals containing tilmicosin at a dose rate of 10 mg/kg. Two other dogs (1 male and 1 female) were injected subcutaneously with microcrystals containing tilmicosin at a dose rate of 20 mg/kg. On the sixth day, lungs, trachea, kidneys, jejunum, samples of dorsal and ventral skin, and a piece of latissimus dorsi muscle were harvested from all animals and a control. Levels of tilmicosin were found in the blood pellet to be greater than 0.5 ppm for about 4.5 days. None of the dogs exhibited any serious negative reactions to the drug. FIG. 3 illustrates levels of tilmicosin in the blood serum and FIG. 4 illustrates levels of tilmicosin in the blood pellet. These figures show the drug associated with the blood cells, and not the serum. "Blood serum" refers to the liquid portion of blood which remains after at least a substantial portion of the blood cells and clotting proteins have been removed. "Blood Pellet" refers to the portion of blood which forms as a pellet following precipitation of at least a substantial portion of the clotting proteins and blood cells following centrifugation.

Figure 5A:
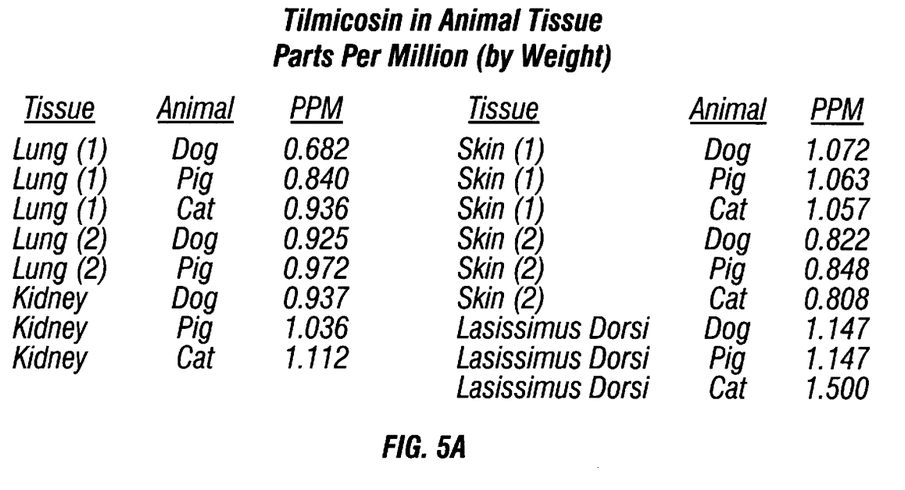
FIG. 5 is a graphical illustration of levels of tilmicosin in six types of body tissue in dogs, pigs, and cats six days after the administration of 20 mg/kg of microcrystals containing tilmicosin. Data is presented in a parts per million v. type of tissue format.
Figure 5B:
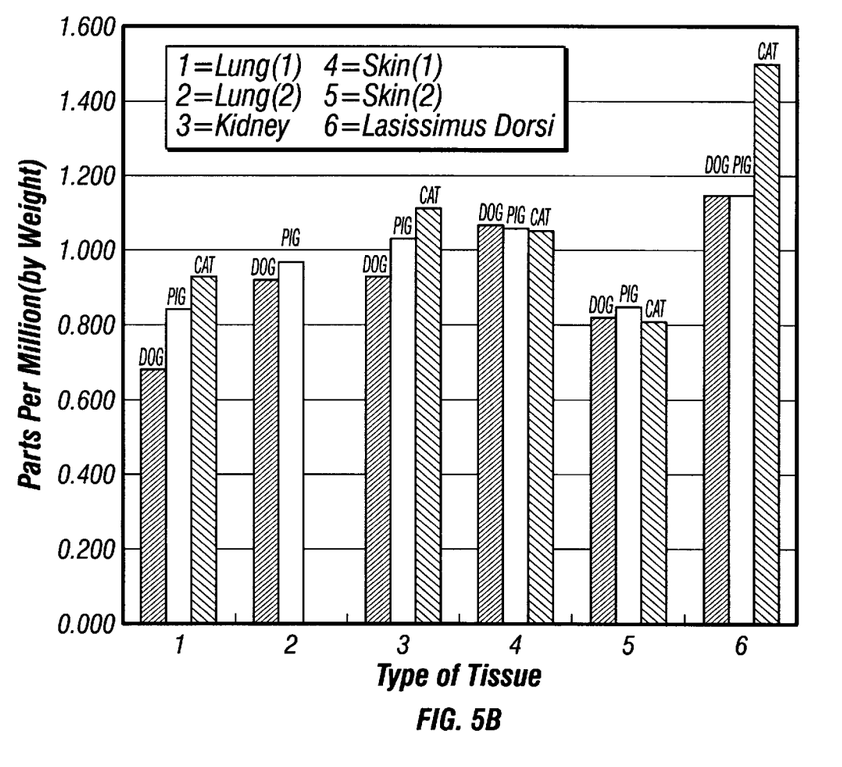

Levels of tilmicosin in the various tissues are illustrated in FIG. 5. This figure shows than high levels of tilmicosin are found in the variety of tissues studied after six days. These results show that the tilmicosin was moving from the blood cells and into the various body tissues.

Two pigs were injected intramuscularly with a dose of 20 mg/kg of microcrystals containing tilmicosin. On the sixth day, lungs, trachea, kidneys, jejunum, samples of dorsal and ventral skin, and a piece of latissimus dorsi muscle were harvested from both animals and a control. Levels of tilmicosin found in the tissues are illustrated in FIG. 5. None of the pigs died as a result of the tilmicosin administration, despite the high dose used.

Two female cats were injected subcutaneously in the dorsal cervical area with a dose of 20 mg/kg of microcrystals containing tilmicosin. No abnormalities were observed over the six-day in-life observation period. On the sixth day, lungs, trachea, kidneys, jejunum, samples of dorsal and ventral skin, and a piece of latissimus dorsi muscle were harvested. Levels of tilmicosin found in the tissues are illustrated in FIG. 5.

EXAMPLE 6

The Use of Tilmicosin Microcrystals to Treat Kennel Cough in Puppies

This example discusses how microcrystals containing tilmicosin were used to treat "kennel cough" in puppies with success. This example also describes a comparison of therapy with tilmicosin microcrystals versus conventional therapy with amoxicillin.

Kennel cough is often accompanied by nasal discharge and cough and is suspected to be of Bordetella brontiseptica origin. Present methods of treating kennel cough suffer from a high incidence of lack of compliance with the requirements of the therapy on the part of the animal owner. Therefore, the present method which offers a therapy which can be administered once a week by an animal caretaker finds great utility. In many instances, complete recovery from the disease will be accomplished with a single administration of the microcrystals suspension.

Five to seven week old puppies of various breeds were used. All were currently showing nasal discharge and some degree of cough on tracheal palpation. Nine puppies were placed in each treatment group.

Puppies in the tilmicosin microcrystals group were dosed at 20 mg/kg in a single subcutaneous injection between the shoulder blades. No serious reactions were observed at the injection sites of puppies treated with tilmicosin microcrystals.

Puppies in the amoxicillin group were treated with Amoxi Drops® (Pfizer) at the recommended dosage of 5 mg/lb twice daily orally. Puppies under 2.5 lbs were given 0.25 cc of 50 mg/cc suspension, and puppies 2.5 lbs–5 lbs were given 0.50 cc of 50 mg/cc suspension. The owner was instructed to repeat the dosage twice daily for the entire week.

After seven days, the puppies were examined. All puppies in the tilmicosin microcrystals group showed no nasal discharge of any type. One puppy still had a very mild cough at this time on tracheal palpation. Six puppies in the amoxicillin group still showed nasal discharge to some degree.

EXAMPLE 7

The Use of Tilmicosin Microcrystals to Treat Respiratory Disease in Cats

This example illustrates how 20% Tilmicosin microcrystals were used to treat upper respiratory infections in cats.

Three cats with upper respiratory infections that were suspected to be at least partially Bacterial were selected for study. The cats were healthy except for the respiratory disease and had no history of previous drug reactions. One cat was treated with tilmicosin microcrystals and was injected subcutaneously in the dorsal cervical area using aseptic technique at a dose of 20 mg/kg. The second cat was treated with clavimox®, which is an approved antibiotic with a label indication for upper respiratory disease. The third cat was untreated.

At the end of seven days the cats were evaluated. The cat treated with tilmicosin microcrystals showed no remaining symptoms. Eyes and nose were clear, and no sneezing or coughing was observed or reported by the owner.

The cat treated with clavimox® showed mild sneezing and/or cough and an elevation in rectal temperature of less than one degree. Ocular and/or nasal discharge was either mild or absent.

The untreated cat showed severe sneezing and coughing, elevated body temperature, and a very evident discharge from the eyes and nose. Appetite was diminished or absent.

EXAMPLE 8

Safe Injection of Flunixin Microcrystals in Dogs and Cats

This example illustrates that microcrystals containing flunixin can be safely injected into dogs and cats.

Two dogs and two cats (both groups containing one male and one female) were selected for study. The animals were injected subcutaneously between the shoulder blades at a dose rate of 20 mg/kg of body weight at Day 0. The animals were observed daily for seven days for signs of toxicity and general health. The female cat had diarrhea on days 2–4. No other abnormalities were observed in any of the other animal.

EXAMPLE 9

Safe Injection of Cefoperozone Microcrystals in Dogs and Cats

This example illustrates that microcrystals containing cefoperozone can be safely injected into dogs and cats.

Two dogs and two cats (both groups containing one male and one female) were selected for study. The animals were injected subcutaneously between the shoulder blades at a dose rate of 20 mg/kg of body weight at Day 0. The animals were observed for signs of toxicity and general health for seven days. No abnormalities were observed in any of the animals.

The following examples illustrate how the manufacturing technology was applied to manufacture microcrystals containing various pharmacologically active compounds on a small scale, using a laboratory scale sonicator or small volume microfluidizer.

The manufacture of microcrystals containing several pharmacologically active compounds is illustrated in the examples set forth below. The examples illustrate some of the problems which may be encountered in workings with a particular drug, and solutions which were devised. The person of skill in the art will see that these solutions, and others which are known in the art, can be applied to successfully manufacture microcrystals of a wide variety of water insoluble compounds.

Those skilled in the art also know of the various techniques which may be applied to cause water soluble compounds to behave more like water insoluble compounds. Therefore, these techniques can also be applied to the manufacture of some water soluble compounds.

EXAMPLE 10

Preparation of Microcrystals Containing Flunixin 11 mg of flunixin was placed into 10 ml of water with good stirring provided by a magnetic stir bar. Very little of the material went into solution even after 10 minutes stirring. The volume was raised to 30 ml with water and less than half of the crystals dissolved into solution. The pH of the suspension was 3.4. The suspension was then titrated to pH 8.4 which caused a change in the shape of the clumps of crystals into floculates on the top of the water but all of the material still did not dissolve.

A flunixin microcrystal suspension was prepared in the following manner; In a 500 ml beaker 90 ml of 300 mM mannitol, 2 mM sodium phosphate buffer was mixed with 30 grams of flunixin and 30 grams phospholipids syrup. The preparation was blended using an Omni GLH homogenizer (which operates according to a "chop and blend" principle) with a medium probe while titrating to pH 5.2. The preparation was then passed through a M-110F Microfluidizer from Microfluidics Corporation, using an inlet pressure of 55 psi resulting in an internal pressure of 1400 psi. An ice water cooling coil bath was used on the outlet port of the microfluidizer to prevent the build up of heat in the preparation. After about 4 passes through the microfluidizer the preparation creamed and became thick. The mixture was then sonicated and an additional 7.5 grams of phospholipids syrup was added to the preparation. After further processing the product demonstrated aggregation of crystals under microscopy. Several more additions of phospholipids syrup were made during processing for a total of 17 grams of additional phospholipid syrup added. The final product appeared to be a homogenous mixture of small crystals that had some tendency to aggregate but with an average particle size of less than 3 µm by microscopy.

EXAMPLE 11

Preparation of Microcrystals of Tilmicosin

A 20% tilmicosin microcrystal reparation was made in the following manner; In a 500 ml beaker 42.4 grams of tilmicosin was mixed with 40 grams of phospholipid syrup and 120 ml of 300 mM mannitol, 2 mM sodium phosphate buffer at pH 8.2. The mixture was then blended using an Omni GLH Homogenizer with a medium probe. The pH of the preparation went to 9.07 and was allowed to remain there. The preparation was then passed a total of 7 times through a M-110F Microfluidizer from Microfluidics Corporation, using an inlet pressure of 55 psi resulting in an internal pressure of 1400 psi. An ice water cooling coil bath was used on the outlet port of the microfluidizer to prevent the buildup of heat in the preparation. The final product appeared as a homogeneous off white suspension of small free flowing crystals with an average particle size of less than 3 $\mu$m by microscopy.

EXAMPLE 12

Preparation of Cephalone Microcrystals

A preparation of cephalone microcrystals was made in the following manner. 30 grams of phospholipids syrup were hydrated in 90 ml of 300 mM mannitol, 2 mM sodium phosphate pH 8.2 for 30 minutes. The mixture was then blended using an Omni GLH homogenizer for 5 minutes while titrating to a pH of 7.10. Next 30 grams of cephalone was added to the preparation and the mixture was blended and titrated to pH 6.75. The mixture was then passed a total of seven times through a M-110F Microfluidizer from Microfluidics Corporation, using an inlet pressure of 55 psi resulting in an internal pressure of 1100 psi. An ice water cooling coil bath was used on the outlet port of the Microfluidizer to prevent the build up of heat in the preparation. The preparation appeared as a homogeneous mixture with a average particle size of less than 3 microns by microscopy.

EXAMPLE 13

Preparation of Nitazoxinide Microcrystals

A preparation of nitazoxanide microcrystals was made in the following manner: 30 grams of phospholipids syrup were hydrated in 90 ml of 300 mM mannitol, 2 mM sodium phosphate pH 8.2 for 30 minutes. The mixture was then blended using a Omni GLH homogenizer for 5 minutes while titrating to a pH of 5.14. Next 30 grams of nitazoxanide was added to the preparation and the mixture was blended and titrated to pH 5.02. The mixture was then passed a total of seven times through a M-110F Microfluidizer from Microfluidics Corporation, using an inlet pressure of 55 psi resulting in an internal pressure of 1100 psi. An ice water cooling coil bath was used on the outlet port of the microfluidizer to prevent the build up of heat in the preparation. The preparation appeared as a homogeneous mixture with a average particle size of lees than 3 $\mu$m by microscopy.

EXAMPLE 14

Preparation of 20% Oflaxacin Microcrystals

A preparation of 20% ofloxacin microcrystals was obtained in the following manner: In a 500 ml beaker 40 grams of ofloxacin was mixed with 40 grams of phospholipids syrup and 120 ml of 300 mM mannitol, 2 mM sodium phosphate buffer at pH 8.2. The mixture was then blended using an Omni GLH homogenizer with a medium probe. The pH of the preparation went to 7.06 and was allowed to remain there. The preparation was then passed a total of seven times through a M-110F Microfluidizer from Microfluidics Corporation, using an inlet pressure of 55 psi resulting in an internal pressure of 1400 psi. An ice water cooling coil bath was used on the outlet port of the microfluidizer to prevent the build up of heat in the preparation. The final product appeared as a homogeneous milky white suspension of small free flowing crystals with an average particle size of less than 3 $\mu$m by microscopy.

EXAMPLE 15

Preparation of Cefaquinolone Microcrystals 30 grams of phospholipid syrup (see Example 1) was hydrated in 90 ml of 300 mM mannitol, 2 mM sodium phosphate, pH 8.2 for 30 minutes. The mixture was then blended using an Omni GLH homogenizer for five minutes while titrating to a pH of 7.10. 30 grams of cefaquinolone was then added to the preparation and the mixture was blended and titrated to pH 6.75. The mixture was then passed a total of seven times through an M-110F Microfluidizer from Microfluidics Corporation, using an inlet pressure of 55 psi resulting in an internal pressure of 1100 psi. An ice water cooling coil bath was used on the outlet port of the microfluidizer to prevent the build up of heat in the preparation. The preparation appeared as a homogeneous mixture with an average particle size of less than 3 $\mu$m by microscopy.

EXAMPLE 16

Preparation of Ofloxacin Microcrystals

In a 100 ml beaker, 4.8 grams of phospholipid syrup (see Example 1) was hydrated in 38.3 ml of 300 mM mannitol, 2 mM sodium phosphate buffer at pH 8.2 for one hour, and then was blended using an Omni GLH homogenizer. Next 4.86 grams of ofloxacin was added to the preparation and the mixture was blended as above. The preparation was then sonicated for 30 minutes using a Sonifier Cell Disrupter from Heat Systems Ultrasonics, cycling the sonicator off for one minute for every 3 minutes sonication time and keeping the preparation immersed in an ice water bath to prevent the build up of heat while being titrated to a pH of 6.87. The resulting preparation appeared as a milky white suspension and had an average particle size of less than 3 $\mu$m.

EXAMPLE 17

Preparation of Microcrystals of Cefoperazone 15 mg of cefoperazone acid was placed in 10 ml of water with good stirring supplied by a magnetic stir bar. Some of the material seemed to dissolve but there was still evidence of undissolved material even after 30 minutes stirring. The suspension resulted in a pH of 3.3. The volume was raised to 30 ml with water and very little more of the precipitate dissolved and the pH remained the same. The suspension was then titrated to pH 8.2 with 50 $\mu$l of 1 M NaOH and there was still evidence of undissolved material.

A preparation of cefoperazone microcrystals was prepared in the following manner; In a 50 ml beaker, 3.0 grams of phospholipids syrup and 6.0 grams of cefoperazone acid was added slowly to 21 ml of 300 mM mannitol, 2 mM sodium phosphate buffer at pH 8.2 with intermittent sonication supplied by a Sonifier Cell Disrupter from Heat Systems Ultrasonics. The preparation was then sonicated for 10 minutes, cycling the sonicator off for one minute for every 3 minutes sonitation time and keeping the preparation immersed in an ice water bath to prevent the build up of heat while being titrated to a pH 4.47. Further additions of 3 grams cefoperazone and 1.5 grams phospholipids syrup were made and sonication was continued for another 20 minutes. The resulting preparation appeared as a milky white suspension and had an average particle size of less than 3 μm by microscopy with less than 10% of the material greater than 3 μm.

While many examples and embodiments of the present invention have been shown and described herein, various modifications may be made without departing from the scope of the present invention, and all such modifications and equivalents are intended to be covered.

Other embodiments of this invention are disclosed in the following claims.

We claim:

1. A pharmaceutical composition comprising microcrystals, the microcrystals comprising a pharmacologically active compound and being contained within a phospholipid layer; wherein
   at least 50 percent of the microcrystals are from about 0.5 μm to about 3.0 μm in diameter; and
   at least about 10 percent of the microcrystals are from about 3.0 μm to about 10 μm in diameter;
      at least about 90% of the micrcocrystals are less than about 10 μm in diameter; and
      the composition contains microcrystals that are greater than about 10 μm in diameter.

2. The composition of claim 1 wherein at least about 0.5% of the microcrystals are greater than about 10 μm in diameter.

3. The composition of claim 1 wherein at least about 1% of the microcrystals are greater than about 10 μm in diameter.

4. The composition of claim 1 wherein
   at least fifty percent of the microcrystals are from about 0.5 μm to about 3.0 μm in diameter;
   from about thirty to about forty percent of the microcrystals are from about 3.0 μm to about 10 μm in diameter; and
   the composition contains microcrystals which are greater than about 10 μm in diameter.

5. The composition of claim 4 wherein at least about 0.5% of the microcrystals are greater than about 10 μm in diameter.

6. The composition of claim 4 wherein at least about 1% of the microcrystals are greater than about 10 μm in diameter.

7. A method for manufacturing a pharmaceutical composition for the sustained release of a pharmacologically active compound, the composition comprising microcrystals of a pharmacologically active compound contained within a phospholipid layer, the method comprising:
   forming a suspension comprising microcrystals of the pharmacologically active compound suspended in a lipid composition; and
   passing the suspension through a homogenizer at high pressure to coat the microcrystals with the lipid composition to produce a composition of microcrystals of a pharmacologically active compound contained within a phospholipid layer, wherein
      at least about 50 percent of the micrcocrystals are from about 0.5 μm to about 3 μm in diameter;
      at least about ten percent of the microcrystals are from about 3 μm to about 10 μm in diameter; and
      the composition contains microcrystals which are greater than about 10 μm in diameter.

8. The method of claim 7 wherein at least about 1% of the microcrystals are greater than about 10 μm in diameter.

9. A method for manufacturing a pharmaceutical composition for the sustained release of a pharmacologically active compound, the composition comprising microcrystals of a pharmacologically active compound contained within a phospholipid layer, the method comprising:
   forming a lipid composition; and
   contacting the lipid composition with the microcrystals to coat the microcrystals with the lipid composition to produce a composition of microcrystals coated with a phospholipid layer wherein
      at least about 50 percent of the microcrystals are from about 0.5 μm to about 3 μm in diameter;
      at least about ten percent of the microcrystals are from about 3 μm to about 10 μm in diameter; and
      the composition contains microcrystals which are larger than about 10 μm in diameter.

10. The method of claim 9 wherein at least about 1% of the microcrystals are greater than about 10 μm in diameter.

11. The method of claim 7 or 10, wherein at least about twenty five percent of the microcrystals are greater than about 3 μm in diameter.

12. The method of claim 7 wherein the composition of lipid and microcrystals is passed through the homogenizer at least two times.

13. The method of claim 7 or 10, wherein the pharmacologically active compound is an antibiotic.

14. The method of claim 13, wherein the antibiotic is oxytetracycline.

15. The method of claim 13 wherein the antibiotic is tilmicosin.

16. The method of claim 13 wherein the antibiotic is a floroquinolone and a cephalosporin covalently combined to form a single molecule.

17. The method of claim 13 wherein the antibiotic is a floroquinolone.

18. The method of claim 17 wherein the floroquinolone is selected from the group consisting of: ofloxacin, sarafloxacin, and ciprofloxacin.

19. The method of claim 13 wherein the antibiotic is a cephalosporin.

20. The method of claim 19 wherein the cephalosporin is cefazolin.

21. The method of claim 19 wherein the cephalosporin is cefuroxime or a derivative of cefuroxime.

22. The method of claim 19 wherein the cephalosporin is cefoperazone.

23. The method of claim 19 wherein the cephalosporin is cefaclor.

24. The method of claim 13 wherein the antibiotic is nitazoxanide.

25. The method of claim 7 or 10, wherein the pharmacologically active compound is an anesthetic.

26. The method of claim 25 wherein the anesthetic is propofal.

27. The method of claims 7 or 10 wherein the pharmacologically active compound is an anti-inflammatory agent.

28. The method of claim 27 wherein the anti-inflammatory agent is flunixin.

29. The method of claims 7 or 10 wherein the pharmacologically active compound is an anti-protozoan agent.

30. The method of claim 29 wherein the anti-protozoan agent is nitazoxanide.

31. The method of claims 7 or 10 further comprising the step of sterilizing the composition of microcrystals.

32. The method of claim 31 wherein the step of sterilizing the composition of microcrystals comprises the use of gamma radiation to sterilize the composition.

33. A method for treating an infection in a mammal comprising the steps of:
   administering to the mammal to be treated an effective dose of a composition of microcrystals, the microcrystals comprising an antibiotic and being contained within a phospholipid layer;
   wherein at least about 50 percent of the microcrystals are from about 0.5 $\mu$m to about 3.0 $\mu$m in diameter;
   wherein at least about ten percent of the microcrystals are from about 3.0 $\mu$m to about 10 $\mu$m in diameter; and
   the composition contains microcrystals that are larger than about 10 $\mu$m in diameter.

34. The method of claim 33 wherein at least about 1% of the microcrystals are larger than about 10 $\mu$m in diameter.

35. The method of claim 33 wherein the antibiotic is selected from the group consisting of: oxytetracycline, tilmicosin, cephalone, a floroquinolone, a cephalosporin, or nitazoxanide.

36. The method of claim 33 wherein the composition is administered to the mammal to be treated by parenteral administration.

37. The method of claim 33 wherein the composition is administered to the mammal to be treated by subcutaneous administration.

38. The method of claims 33–35 wherein the mammal is a bovine.

39. The method of claims 33–35 wherein the mammal is an equine.

40. The method of claims 33–35 wherein the mammal is selected from the group consisting of: porcines, canines, and felines.

41. The method of claims 33–35 wherein the infection is caused by a protozoan.

42. A method for treating respiratory disease in a mammal comprising the steps of:
   administering to the mammal to be treated an effective dose of a composition of microcrystals, the microcrystals comprising an antibiotic contained within a phospholipid layer; wherein
   at least about 50 percent of the microcrystals are from about 0.5 $\mu$m to about 3.0 $\mu$m in diameter;
   at least about ten percent of the microcrystals are from about 3.0 $\mu$m to about 10 $\mu$m in diameter; and
   the composition contains microcrystals that are larger than about 10 $\mu$m in diameter.

43. The method of claim 42 wherein at least about 1% of the microcrystals are larger than about 10 $\mu$m in diameter.

44. The method of claim 42 wherein the antibiotic is selected from the group consisting of: oxytetracycline, tilmicosin, cephalone, a floroquinolone, a cephalosporin, or nitazoxanide.

45. The method of claim 42 wherein the composition is administered to the mammal to be treated by parenteral administration.

46. The method of claim 42 wherein the composition is administered to the mammal to be treated by subcutaneous administration.

47. The method of claims 42–44 wherein the mammal is a bovine.

48. The method of claims 42–44 wherein the respiratory disease is bovine respiratory disease.

49. The method of claim 42–44 wherein the microcrystals contain oxytetracycline.

50. The method of claims 42–44 wherein the mammal is an equine.

51. The method of claims 42–44 wherein the mammal is selected from the group consisting of: porcines, canines, and felines.

52. A method for treating inflammation in a mammal comprising the steps of:
   administering to the mammal to be treated an effective dose of a composition of microcrystals, the microcrystals comprising an anti-inflammatory agent and being contained within a phospholipid layer; wherein
   at least about 50 percent of the microcrystals are from about 0.5 $\mu$m to about 3.0 $\mu$m in diameter;
   at least about ten percent of the microcrystals are from about 3.0 $\mu$m to about 10 $\mu$m in diameter; and
   the composition contains microcrystals that are larger than about 10 $\mu$m in diameter.

53. The method of claim 52 wherein at least about 1% of the microcrystals are larger than about 10 $\mu$m in diameter.

54. The method of claim 52 wherein the composition is administered to the mammal to be treated by parenteral administration.

55. The method of claim 52 wherein the composition is administered to the mammal to be treated by subcutaneous administration.

56. The method of claims 52 or 53 wherein the anti-inflammatory agent is flunixin.

57. A method for treating pain in a mammal comprising the steps of:
   administering to the mammal to be treated an effective dose of a composition of microcrystals, the microcrystals comprising an anesthetic and being contained within a phospholipid layer; wherein
   at least about 50 percent of the microcrystals are from about 0.5 $\mu$m to about 3.0 $\mu$m in diameter;
   at least about ten percent of the microcrystals are from about 3.0 $\mu$m to about 10 $\mu$m in diameter; and
   the composition contains microcrystals that are greater than about 10 $\mu$m in diameter.

58. The method of claim 57 wherein at least about 1% of the microcrystals are greater than about 10 $\mu$m in diameter.

59. The method of claim 57 wherein the composition is administered to the mammal to be treated by parenteral administration.

60. The method of claim 57 wherein the composition is administered to the mammal to be treated by subcutaneous administration.

61. The method of claims 57 or 58 wherein the anesthetic is propofal.

* * * * *

UNITED STATES PATENT AND TRADEMARK OFFICE
CERTIFICATE OF CORRECTION

PATENT NO.   : 6,180,136 B1
DATED        : January 30, 2001
INVENTOR(S)  : Kenneth A. Larson, William R. Campbell and Douglas I. Hepler.

It is certified that error appears in the above-identified patent and that said Letters Patent is hereby corrected as shown below:

Column 1,
Line 21, delete "he' and insert therefor -- be --.

Column 2,
Line 23, delete "di closes" and insert therefor -- discloses --.
Line 51, delete "caninee" and insert therefor -- canines --.

Column 3,
Line 22, delete "microcryetals" and insert therefor -- microcrystals --.
Line 54, delete "phoslhatidylcholine" and insert therefor -- phosphatidylcholine --.
Line 55, delete "wieight" and insert therefor -- weight --.

Column 5,
Line 26, delete "aid" and insert therefor -- and --.
Line 41, delete "carborylic' and insert therefor -- carboxylic --.

Column 7,
Line 57, delete "fox" and insert therefor -- for --.
Line 59, delete "microcrystal" and insert therefor -- microcrystals --.

Column 8,
Line 9, delete "tendered" and insert therefor -- rendered --
Line 28, delete "die" and insert therefor -- due --.
Line 56, delete "3.0" and insert therefor -- 30 --.

Column 9,
Line 53, delete "Water" and insert therefor -- water --.
Lines 61-62, delete "manufactufer's" and insert therefor -- manufacturer's --.

Column 11,
Line 23, delete "phoslholipid" and insert therefor -- phospholipid --.

Column 12,
Line 23, delete "homogenize," and insert therefor -- homogenizer, --.

UNITED STATES PATENT AND TRADEMARK OFFICE
CERTIFICATE OF CORRECTION

PATENT NO. : 6,180,136 B1
DATED : January 30, 2001
INVENTOR(S) : Kenneth A. Larson, William R. Campbell and Douglas I. Hepler.

It is certified that error appears in the above-identified patent and that said Letters Patent is hereby corrected as shown below:

Column 14,
Line 22, delete "than" and insert therefor -- that --.

Column 16,
Line 66, delete "reparation" and insert therefor -- preparation --.

Column 19,
Line 24, delete "micrcocrystals" and insert therefor -- microcrystals --.
Line 62, delete "micrcocrystals" and insert therefor -- microcrystals --.

Signed and Sealed this

Twenty-fifth Day of September, 2001

Attest:

*Nicholas P. Godici*

NICHOLAS P. GODICI
*Attesting Officer*   *Acting Director of the United States Patent and Trademark Office*